(12) United States Patent
Zochowski et al.

(10) Patent No.: US 11,253,400 B2
(45) Date of Patent: Feb. 22, 2022

(54) NEGATIVE PRESSURE WOUND APPOSITION DRESSING SYSTEM

(71) Applicant: Midwest Training and Development Services, LLC, Indianapolis, IN (US)

(72) Inventors: Christopher G. Zochowski, New Albany, OH (US); Keith R. Berend, New Albany, OH (US)

(73) Assignee: MIDWEST TRAINING AND DEVELOPMENT SERVICES, LLC, Indianapolis, IN (US)

( * ) Notice: Subject to any disclaimer, the term of this patent is extended or adjusted under 35 U.S.C. 154(b) by 172 days.

(21) Appl. No.: 16/386,427

(22) Filed: Apr. 17, 2019

(65) Prior Publication Data

US 2019/0350764 A1    Nov. 21, 2019

Related U.S. Application Data

(60) Provisional application No. 62/672,283, filed on May 16, 2018.

(51) Int. Cl.
*A61M 1/00* (2006.01)
*A61F 13/00* (2006.01)
*A61F 13/02* (2006.01)

(52) U.S. Cl.
CPC ..... *A61F 13/00068* (2013.01); *A61M 1/0003* (2013.01); *A61M 1/90* (2021.05);
(Continued)

(58) Field of Classification Search
CPC .............. A61F 13/00068; A61F 13/023; A61F 2013/00174; A61F 2013/00536; A61M 1/0088; A61M 1/0003; A61M 1/0031
See application file for complete search history.

(56) References Cited

U.S. PATENT DOCUMENTS 4,876,894 A * 10/1989 Heller ................. G01L 19/0007
73/756
8,057,449 B2    11/2011 Sanders et al.
(Continued)

FOREIGN PATENT DOCUMENTS

WO      2014174218 A1    10/2014
WO    WO-2015061352 A2 *  4/2015    ....... A61F 13/00068

OTHER PUBLICATIONS

Storm et al., Simplified Negative Pressure Wound Therapy Device For Application in Low-Resource Settings, J Orthorp Trauma, Oct. 29, 2015, pp. 1-9.

*Primary Examiner* — Philip R Wiest
*Assistant Examiner* — Gregory J Feulner
(74) *Attorney, Agent, or Firm* — C. John Brannon; Brannon Sowers & Cracraft PC

(57) ABSTRACT

The present disclosure relates generally to the field of medical treatment and therapy of mammalian tissue. More specifically, it relates to coverings and/or dressings that provide negative pressure at mammalian tissue sites, such as at one or more sites of surgical, non-surgical, and/or traumatic wounds, to promote closure and healing of the wounds. A key embodiment of the disclosed invention entails the use of a dressing that comprises a sponge that is shaped so as to create a vector force inward bringing wound edges together to promote healing, especially upon application of negative pressure. Other key features of the disclosed invention are its simplicity, its low cost, and that it is completely mechanical and lacks the need for any electronic components. The disclosure also relates to devices, systems, kits and methods for providing said negative pressure at said mammalian tissue sites and promote healing.

17 Claims, 10 Drawing Sheets

(52) U.S. Cl.
CPC ... *A61F 13/023* (2013.01); *A61F 2013/00174* (2013.01); *A61F 2013/00536* (2013.01); *A61M 1/74* (2021.05)

(56) References Cited

U.S. PATENT DOCUMENTS

| | | |
|---|---|---|
| 8,974,428 B2 | 3/2015 | Freedman et al. |
| 9,138,515 B2 | 9/2015 | Locke et al. |
| 9,173,777 B2 | 11/2015 | Zurovcik |
| 2007/0032762 A1* | 2/2007 | Vogel .................. A61M 1/0031 604/305 |
| 2007/0185463 A1 | 8/2007 | Mulligan |
| 2012/0316538 A1 | 12/2012 | Heiser et al. |
| 2013/0296816 A1 | 11/2013 | Greener |
| 2015/0157774 A1* | 6/2015 | Zamierowski ...... A61M 1/0086 601/6 |
| 2018/0140753 A1 | 5/2018 | Askem et al. |
| 2018/0214313 A1 | 8/2018 | Pratt et al. |
| 2019/0209382 A1* | 7/2019 | Locke ..................... A61F 13/02 |

* cited by examiner

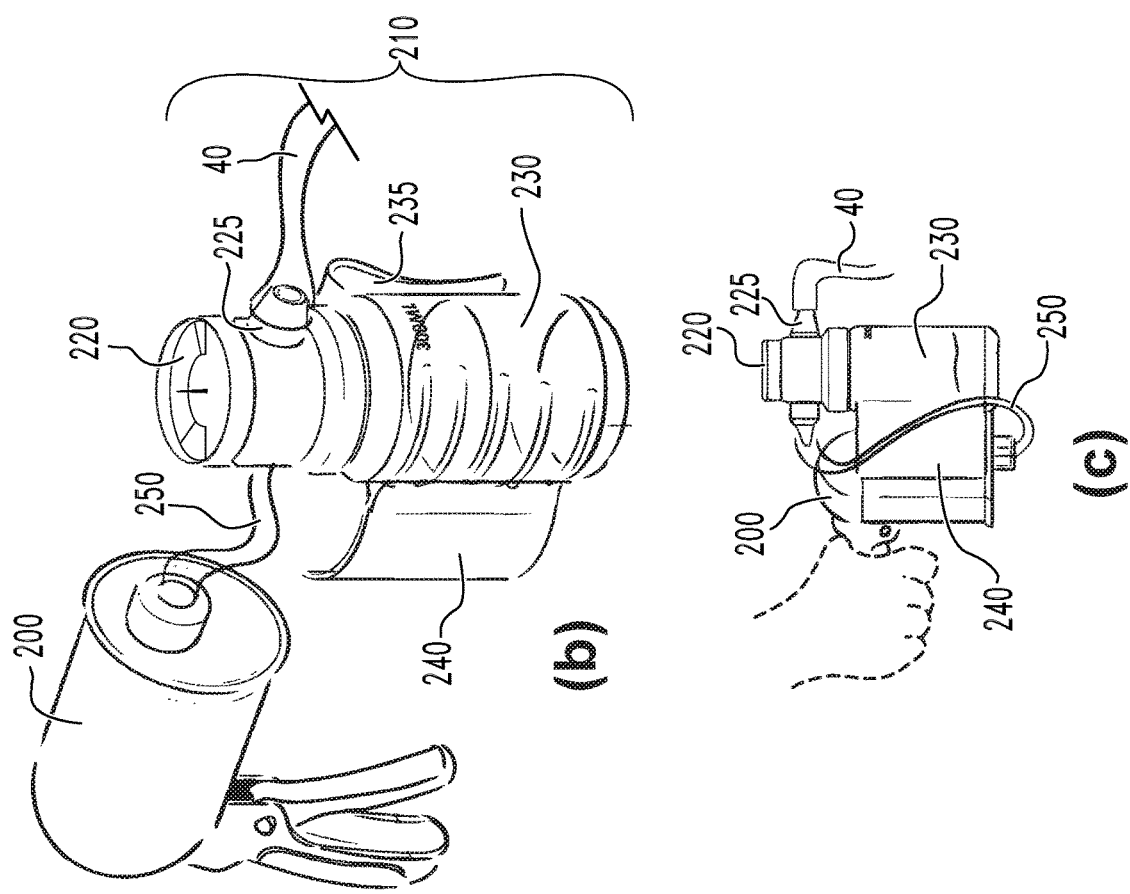
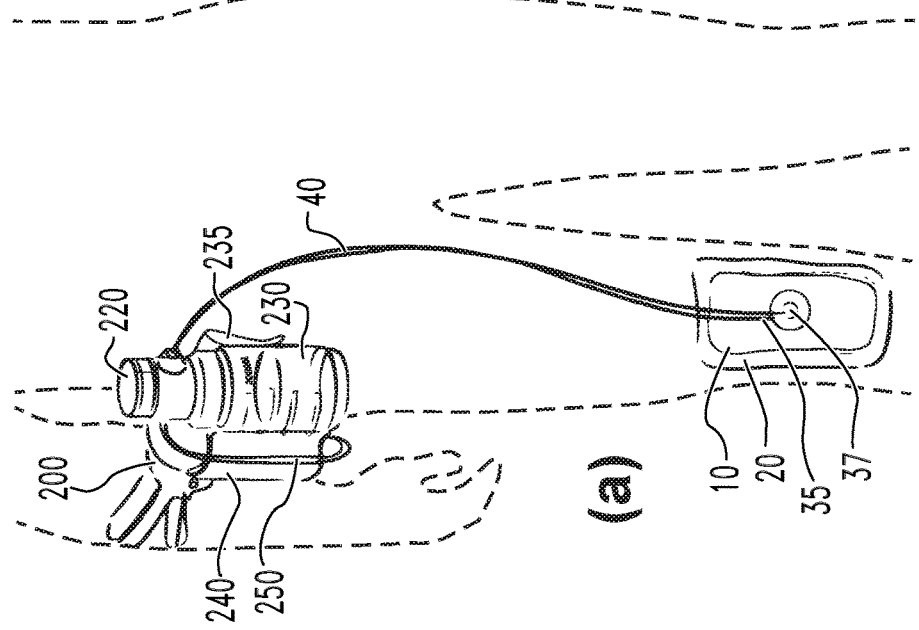
FIG. 7

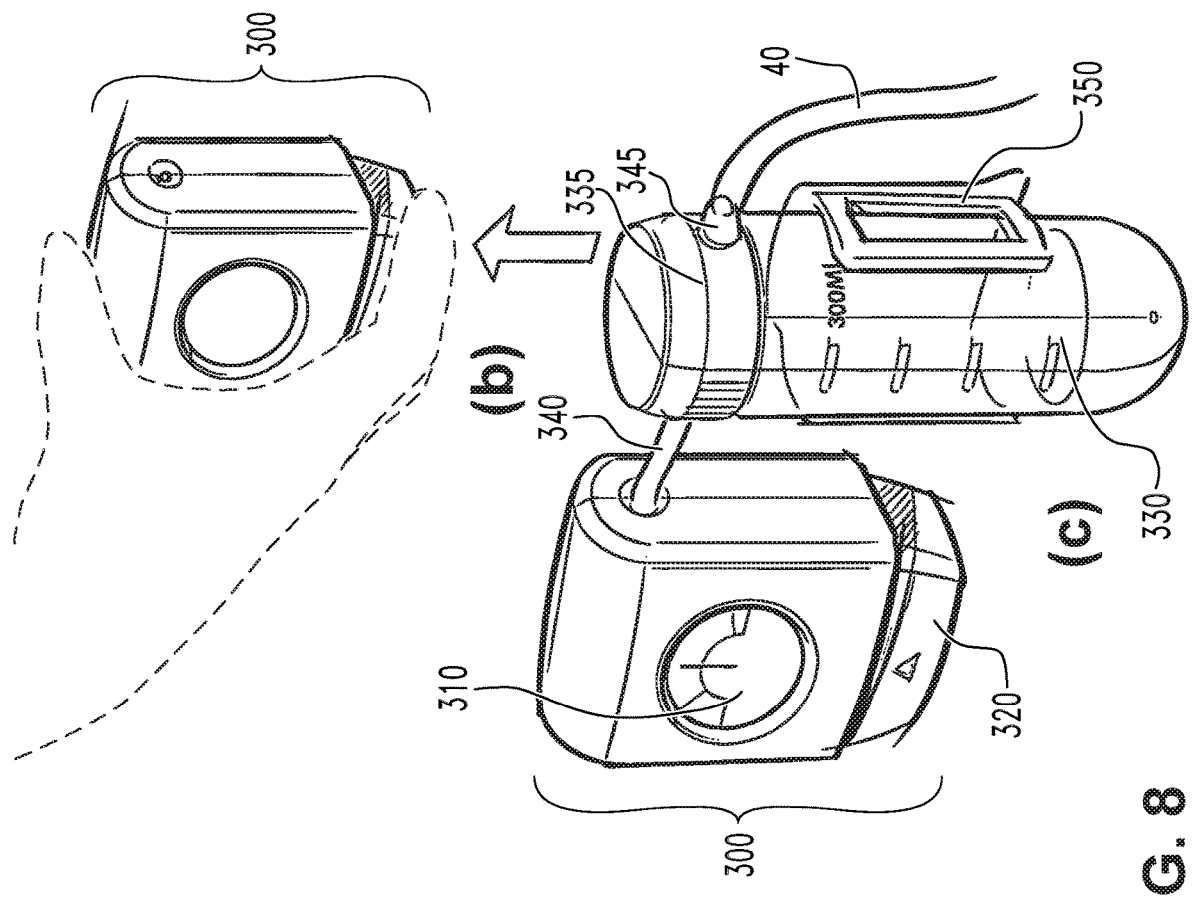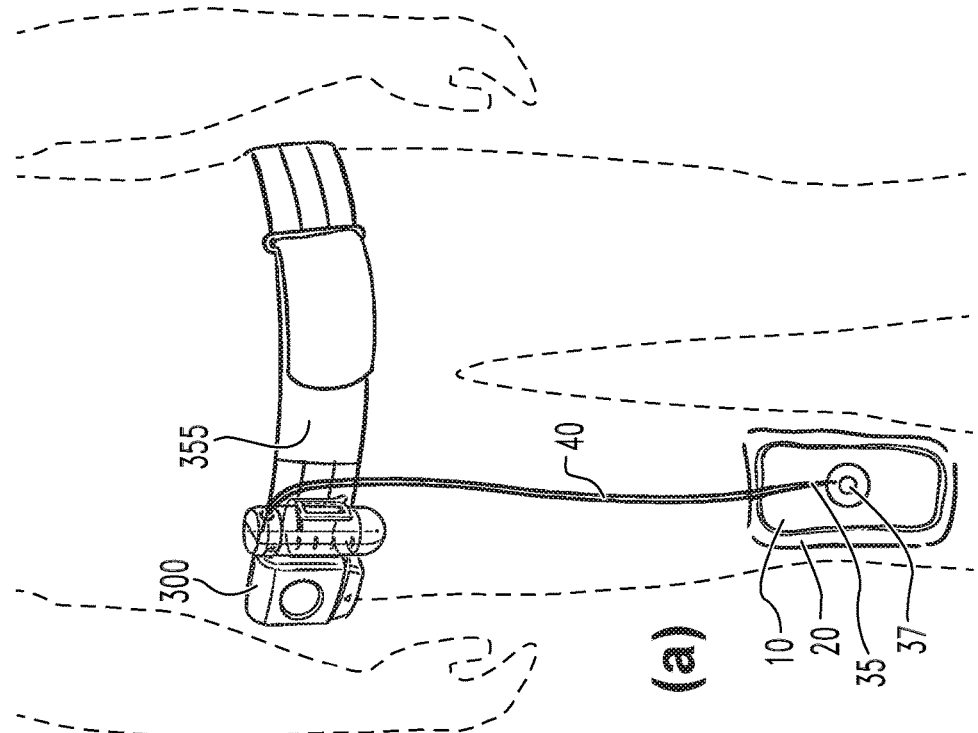
FIG. 8

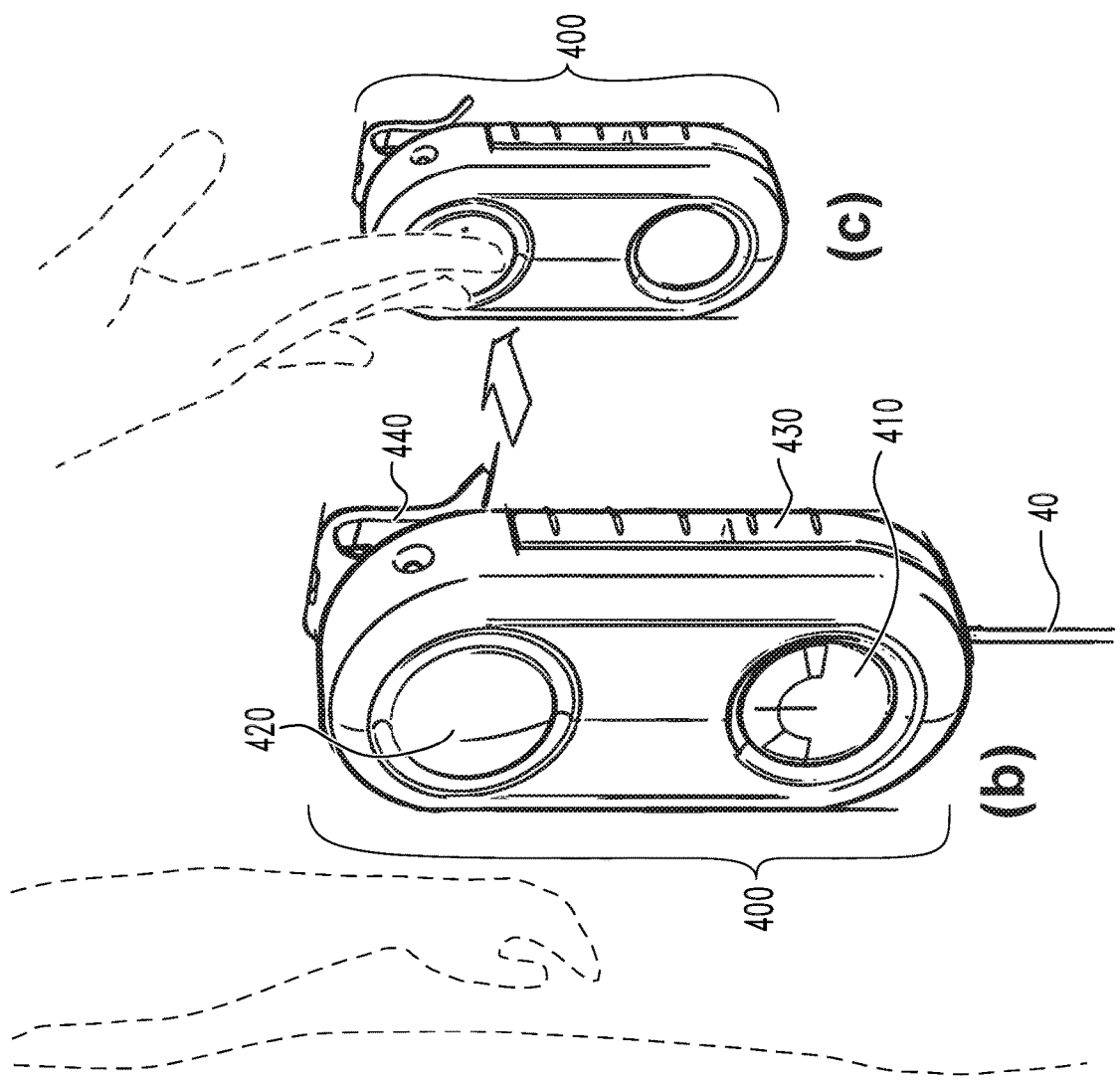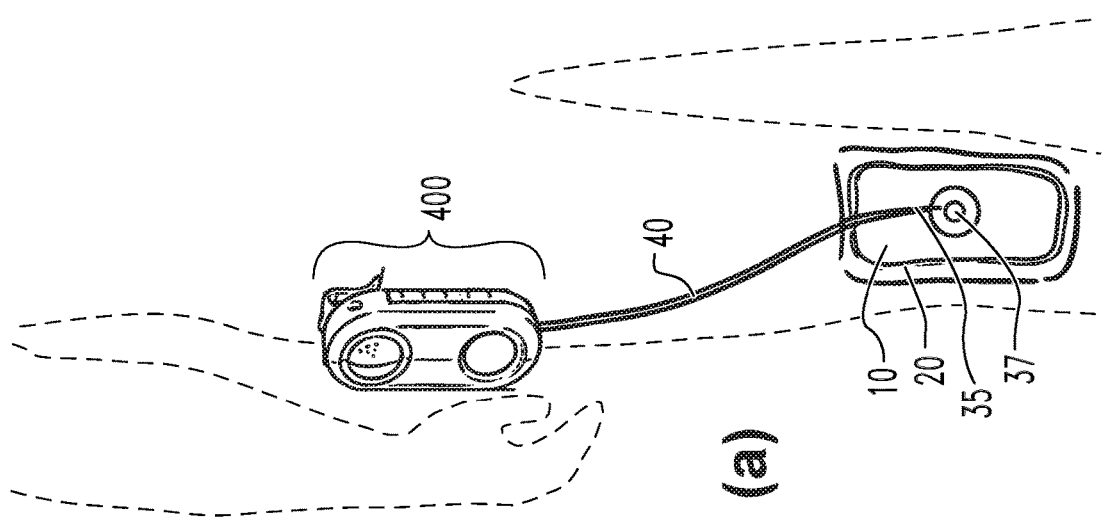
FIG. 9

NEGATIVE PRESSURE WOUND APPOSITION DRESSING SYSTEM

CROSS-REFERENCE TO RELATED APPLICATIONS

This application claims priority under 35 USC § 119(e) to U.S. Provisional Patent Application Ser. No. 62/672,283, filed on May 16, 2018, the disclosure of which is incorporated herein by reference in its entirety.

FIELD OF INVENTION

The present disclosure relates generally to the field of medical treatment and therapy of mammalian tissue. More specifically, it relates to coverings and/or dressings that provide negative pressure at mammalian tissue sites, such as at one or more sites of surgical, non-surgical, and/or traumatic wounds, to promote closure and healing of the wounds. The disclosure also relates to a device, system, and method for providing said negative pressure at said mammalian tissue sites.

BACKGROUND OF INVENTION

Although the invention disclosed in the following pertains primarily to treatment and therapy of wounds in mammalian subjects via the application of negative pressure, it is to be understood that, as contemplated herein, the invention may have general usefulness in the medical treatment and therapy of certain non-wound conditions of mammalian tissue that could benefit from the application of negative pressure.

Negative-pressure wound therapy (NPWT) is a therapeutic technique that uses a vacuum covering and/or dressing to promote healing in acute or chronic wounds and enhance healing, illustratively, of surgical, non-surgical, and traumatic wounds, of second- and third-degree burns, and the like. This therapy involves the controlled application of sub-atmospheric pressure to the local wound environment, using a sealed wound covering and/or dressing connected to a vacuum source. The use of this technique in wound management increased dramatically over the last several decades, and numerous studies have been published to-date examining NPWT. For example, it has been reported that NPWT appears to be useful for treatment of diabetic ulcers, for management of the open abdomen (laparotomy), as well as for other wound types.

Wound healing has been found by many studies to be improved with application of negative pressure. Thus, NPWT promotes wound healing by applying a vacuum through a special sealed covering and/or dressing. It has been observed that the continued vacuum draws out fluid from the wound and increases blood flow to the area. The vacuum may be applied continuously or intermittently, depending on the type of wound being treated and the clinical objectives. Typically, the covering or dressing may have to be changed two to three times per week, or fewer times in some cases. Some of the coverings or dressings used for the technique include open-cell foam dressings and gauze, sealed with an occlusive dressing intended to contain the vacuum at the wound site. Some NPWT devices allow delivery of fluids, such as saline or antibiotics to irrigate the wound, in which case intermittent removal of used fluid supports the cleaning and drainage of the wound bed. Examples of some commercially available NPWT devices include the PREVENA™ Incision Management System (by Acelity™), the V.A.C.Ulta™ Negative Pressure Wound Therapy System (also by Acelity™), and the PICO™ Single Use Negative Pressure Wound Therapy System (by Smith and Nephew).

It has been reported that the negative pressure is found to be optimized between about −120 mmHg and about −150 mmHg. If the negative pressure is too great, the terminal capillaries collapse. If the negative pressure is too slight, there is no benefit observed. Some of the observed advantages of using these vacuum devices include the following. (1) The ability for wound dressing changes to be done less frequently, so that the vacuum needs to be changed only once or twice a week. (2) The suction device keeps the wound free of exudate and lowers the bacterial load. (3) The device keeps grafts, such as skin grafts, unperturbed while healing; and acts as a splint on the graft. (4) Improved oxygenation of the tissues from the negative pressure. (5) The plastic drape acts as a "truss" to keep the wound from splitting or spreading. (6) The wound vacuum can be placed on in a sterile environment, protecting the wound from the bacteria of the environment. (7) Less pain is experienced at the wound site. (8) Protection of the wound from moisture (e.g., stomach overhanging on a hip wound).

A general technique employed in current NPWT treatments usually entails protecting the periwound by applying a skin barrier followed by a transparent film. A dressing or filler material is then fitted to the contours of the wound, which is covered with a non-adherent dressing film, and the overlying foam is then sealed with a transparent film. A drainage tube is connected to the dressing through an opening of the transparent film. A vacuum tube is connected through an opening in the film drape to a canister on the side of a vacuum pump or vacuum source, turning an open wound into a controlled, closed wound while removing excess fluid from the wound bed to enhance circulation and remove wound fluids. This creates a moist healing environment and reduces edema. There must be an air tight seal for this therapy to be successful. The technique is usually used especially with chronic wounds or wounds that are expected to present difficulties while healing.

With current NPWT systems, various types of filler material are available to be used over the wound surface, most usually including the following three types of filler material: (1) open-cell foam; (2) gauze and transparent film; or, (3) honeycombed textiles with a dimpled wound contact surface. In the first type, foam dressings are used to fill open cavity wounds and can be cut to size to fit wounds; the foam dressing is applied, filling the wound, and then a film drape is applied over the top to create a seal around the dressing. In the second type, open weave cotton gauze can be covered with a transparent film, and a flat drain is sandwiched in gauze and placed onto the wound; the film drape covers the wound and creates a complete seal, and then the drain is connected to the pump via the tubing. The third type includes layers of non-woven polyester, joined by a silicone elastomer, and has a non-adherent wound contact surface made up of numerous small semi-rigid dome structures. With all three techniques, once the dressing is sealed, the vacuum pump can be set to deliver continuous or intermittent pressures, with levels of pressure dependent on the device used; and the pressure can be applied constantly or intermittently. The dressing type used depends on the type of wound, clinical objectives, and the patient. For pain sensitive patients with shallow or irregular wounds, wounds with undermining or explored tracts or tunnels, gauze may be used, while foam may be cut easily to fit a patient's wound that has a regular contour and perform better when aggressive granulation formation and wound contraction is the desired goal.

The foregoing notwithstanding, the current NPWT devices available on the market have many shortcomings and downfalls. For example, some available NPWT devices do not include any fluid reservoir to collect fluids. They may include a battery operated electronic pump. They are bulky, expensive, and noisy, bothersome to patients. Furthermore, many types are permeable to gases and fluids, and/or do not provide enough suction to be sufficiently beneficial toward wound healing. Physicians and other medical professionals often report that these devices can be very cumbersome to use, are prone to failure due to discharged batteries, and are costly for insurance and manufacturers. Some patients must pay thousands of dollars out-of-pocket for the use of these devices. The vacuum devices usually have a central pump unit that is powered by a rechargeable battery. There is also a sponge and film that create a closed circuit. The suction device is usually a rigid circular tube and the interface with the sponge is usually made of firm plastic. The rigid plastic and round tubing have been known to occasionally cause pressure and pressure necrosis underneath, which are outcomes that are opposite to the goal of using a vacuum device. In addition, the current vacuum devices have been known to fail quite often. This can be due to a patient that lacks the savviness to recharge the unit, or simply due to a faulty unit. When a vacuum device fails, the result is very poor for wound healing, as a wet sponge stays placed on the incision for a prolonged period of time, possibly up to a week. Also, patients often do not realize when the collection canister is full, which may cause the vacuum to fail. In addition, the canisters may have a good deal of stagnant fluid within, which can create the stigma of an odor. The fluid or exudate that accumulates is rife with bacteria, chemical messengers, and cellular debris. Furthermore, the vacuum devices are often used repeatedly and are often refurbished. They are reportedly cleaned between uses, but there are simply too many crevices and parts for these to not harbor bacteria from the prior users. It is not unusual for physicians and other medical professionals to waste much time in the operating room trying to troubleshoot a vacuum device, only to find out that it was a faulty refurbished unit.

Many apparatuses and systems employing NPWT have been reported to-date that attempt to solve some of the above needs. Examples of these reports include the following: Heiser, J., et al., US Patent Application Publication 2012316538; Askem, B. A., et al., WO Patent Application Publication 2016188968; Greener, B., US Patent Application Publication 2013296816; Locke, C. B., et al., U.S. Pat. No. 9,138,515; Freedman, B. A., et al., U.S. Pat. No. 8,974,428; Zurovcik, D., U.S. Pat. No. 9,173,777; Mulligan, S., US Patent Application Publication 2007185463; Renard, S. et al., WO Patent Application Publication 2014174218; Sanders, T. B., et al., U.S. Pat. No. 8,057,449; Pratt, B. A., et al., WO Patent Application Publication 2017040045 to; and, Storm, K., et al., J. Orthop. Trauma., 29(0 10):533-536 (2015 Oct. 1). However, these, and numerous others like them, suffer from a variety of unfavorable and limiting features, making them costly to produce and/or purchase, and/or potentially impractical or cumbersome to use. Accordingly, there is an ongoing need for simple and versatile dressings, and associated devices, systems, and methods, that provide treatment and therapy of wounds via negative pressure to promote closure and healing of the wounds. Disclosed in the following is a simple, practical, economical negative pressure dressing, device and system that solve the foregoing shortcomings.

SUMMARY OF INVENTION

In one embodiment, the present disclosure provides a negative pressure wound apposition dressing, device and system useful for closure and promoting healing of surgical, non-surgical, and traumatic wounds, and the like. One key aspect of said dressing, device and system is that they are completely mechanical, and do not include any electronic parts or require the use of any electronic sources. In another aspect, said dressing, device and system provide the benefit of negative pressure promotion of tissue oxygenation. In another aspect, said dressing, device and system are adaptable to be used in a modular manner. In another aspect, said negative pressure wound apposition dressing, device and system are designed to be easily operated by the patient when that is desired or required.

Another embodiment of the invention provides a dressing that is flexible, and that comprises a vacuum sponge or porous material (hereinafter referred to simply as "sponge"). The sponge may be made of any suitable porous material commonly used in the medical arts in the treatment of wounds or incisions. This sponge is not rectangular or flat like the sponges in existing products. Instead, the sponge of the invention is designed to have a geometric shape that has the tendency to create an overall vector of force inward (as discussed below), such that when the sponge is placed on a wound or incision, this shape helps draw the wound edges in, and thus take the tension off of the wound, and more so when a negative pressure is applied. For example, the sponge of the invention may be shaped to have a semicircular cross-section, so that when negative pressure is applied, an apposition force will result, and tension on the wound will decrease. While not intended to limit the invention in any way or to imply any limitations on the relative length, width, thickness or other dimensions of the sponge, it may be helpful to envision the sponge as having a shape akin to that of a swimming pool "noodle" cut in half lengthwise, which may or may not be hollow in the middle. The sponge may be shaped so that the lateral cross-section looks like a semi-circular "right-side-up arch" or an "upside-down arch" similar in theory to a shaped charge in the military.

In another embodiment, the sponge of the invention may be designed to be dispensed in a sterile "tape-like" dispenser in various lengths, such as, illustratively, via a roll of dressing. Additionally, the sponge may be designed to be modular, to permit increasing of the length to any needed length or shape. Moreover, if needed, the sponge may optionally be impregnated with one or more agents, antiseptics, antibiotics and/or other medications, such as, illustratively, Ag ions, chlorhexidine, and the like.

In another embodiment, the invention comprises a drape, made of plastic or other suitable material, including occlusive, clear materials; this drape goes over and overlies the sponge. In one aspect, this drape may be designed to possess, either partially or wholly, an "accordion-like" shape; this accordion-like shape would also help to draw the wound edges inwardly and provide further reduction in wound tension and apposition of the wound edges, enhancing the healing process. Additionally, the invention comprises an adhesive tape edge along the edges of the dressing, similar to the adhesive tape edge in existing NPWT devices; when the dressing is positioned over the wound, this adhesive tape edge would run parallel to the wound and would provide a seal along the length of the dressing.

In another embodiment, the invention comprises a means by which the sponge and tape/apron may be provided as a long roll, such as, illustratively, a roll resembling rolled-up insulation for a building, and the like. A suction/pad interface would be designed to be positioned at the beginning of the long roll, which may be unrolled quickly on the wound. The invention may also comprise a "peel-away" layer on the back of the apron making the apron stick to the skin. If the need arises to change the location of the suction/pad interface, then the dressing can be readily cut and sealed with any type of available, inexpensive medical dressing, such as the transparent medical dressings manufactured by 3M known as Tegaderm™, which are typically found in every operating room. In addition, if the need for a longer dressing arises, these can then be lined in a "daisy chain" manner via the use of a Tegaderm™.

In another embodiment, the invention comprises a length of vacuum or suction tubing leading from the dressing sponge to the vacuum source. One important aspect is that the junction of the vacuum tubing to the sponge strip is designed to be rectangular and flat so as to decrease the pressure exerted by the junction and tubing on the wound, which cause pressure and pressure necrosis underneath. In many instances wounds may experience some sort of pressure, such as, illustratively, from the weight of an overhanging stomach, clothing, or an ACE wrap. Thus, in this invention the tubing in the critical area is flat and stented open with a small amount of the same sponge material, so as to decrease pressure on the wound. Beyond the critical area, the tubing may be more rigid.

In another embodiment, the vacuum tubing comprised in the invention is fitted at its end with a valve, such as a one-way valve, illustratively the "duck bill valve" contained in a Jackson-Pratt drain (also called a JP drain). The JP drain is a closed-suction medical device that is commonly used as a post-operative drain for collecting bodily fluids from surgical sites; it consists of an internal drain connected to a grenade-shaped bulb via plastic tubing. While it is not possible to list herein all the plethora of types of valves known in the art that are suitable for the invention herein, a few representative types are listed in the following for the purpose of illustration, such as the medical one-way check valves available from Qosina (e.g., Qosina part numbers 80503, 80130, and 80192; also see: https://www.qosina.com/check-valves), and the like. The collection device may be a bag or another type of canister similar to those used in existing drains, such as the Hemovac® drain available from Zimmer Biomet. The collection device would collect the fluid, and can be emptied easily by the patient, care provider or medical professional via an openable port at the bottom. Most commercial vacuum devices have a disposable collection canister.

In another embodiment, the invention comprises a hand pump as the vacuum source to provide the reduced pressure, which would be created by the hand of the patient, care provider, or medical professional. Illustratively, the hand pump may be similar to that of the rubber bulb of a common stethoscope. Other examples of suitable hand pumps include the pumping mechanisms of a large variety of hand pump types known in the art. While it is not possible to list herein all the suitable types of hand pumps known in the art, a few representative types are listed in the following for the purpose of illustration: the Medical Sputum Aspirator manual suction pump, the "Ambu® Res-Cue" pump suction unit, the VBM Manual Suction Pump, the pistol grip hand pump, the hand pumps used with food storage containers, and the like. Additionally, the hand pump, such as, illustratively, in the case where said hand pump resembles the rubber bulb of a stethoscope, includes a one-way relief or regulator valve that regulates the negative pressure to between a lower and an upper limit. Herein, the lower and upper pressure limits may be between about −120 mmHg and about −150 mmHg. The pressure relief valve is typically positioned by attaching it between the stem of the hand pump and the vacuum tube. The valve is designed to "blow out" if the reduced pressure should exceed the desired set value, such as, illustratively, −150 mmHg. The regulator valve is also designed to make an audible sound if the reduced pressure drops below a certain set value, such as, illustratively, −120 mmHg. The hand pump is used to restore and/or maintain the reduced pressure to between the desired lower and upper reduced pressure limits. Importantly, the hand pump and regulator valve parts of the invention do not include or need to have any electronic parts. Indeed, as stated earlier, the entire invention disclosed herein is completely mechanical and does not include or need any electronic parts or power sources.

In another embodiment, disclosed herein is a method of use of the negative pressure wound apposition dressing, device and system of the invention. This method comprises the steps outlined in the Detailed Description section below.

The foregoing embodiments of the invention, and additional embodiments, are described in greater detail in the Detailed Description section below.

All publications cited throughout this application are incorporated herein by reference in their entirety. Indeed, throughout this description, including the foregoing description of related art and cited publications, as well as any and all publications cited in what follows below, it is to be understood that any and all publicly available documents described herein, including any and all cited U.S. patents, patent applications, and non-patent publications, are specifically incorporated by reference herein in their entirety. Nonetheless, the related art and publications described herein are not intended in any way as an admission that any of the documents described therein, including pending U.S. patent applications, are prior art to embodiments of the present disclosure. Moreover, the description herein of any disadvantages associated with the described products, methods, and/or apparatus, is not intended to limit the disclosed embodiments. Indeed, embodiments of the present disclosure may include certain features of the described products, methods, and/or apparatus without suffering from their described disadvantages.

Naturally, further objects, advantages and features of the present invention are disclosed throughout other areas of the specification, and will become apparent from the following detailed description, claims, and the accompanying drawings.

DESCRIPTION OF DRAWINGS

The foregoing summary, as well as the following detailed description of the preferred embodiments of the invention, will be better understood when read in conjunction with the accompanying figures, in which:

FIG. 7 is a schematic that shows the design of FIG. 6(a) as illustratively being used in conjunction with a suction tubing and dressing assembly of the invention applied to the knee wound of a patient.

FIG. 8 is a schematic that shows the design of FIG. 6(b) as illustratively being used in conjunction with a suction tubing and dressing assembly of the invention applied to the knee wound of a patient.

FIG. 9 is a schematic that shows the design of FIG. 6(c) as illustratively being used in conjunction with a suction tubing and dressing assembly of the invention applied to the knee wound of a patient.

DETAILED DESCRIPTION

Before the present details of the invention are disclosed and described, it is to be understood that this invention is not limited to the specific components, methods, and implementation, or to the precise arrangements and instrumentalities shown, as such may, of course, vary while remaining within the scope and spirit of the invention. It is also to be understood that the terminology used herein is for the purpose of describing particular implementations only, and to assist in understanding the disclosure, and is not intended to be limiting.

The figures illustrating the negative pressure wound apposition dressing, device and system of the invention show some mechanical elements that partially or fully resemble standard mechanical elements used in the art and that will be recognized by one skilled in the art. The detailed descriptions of these elements are presented herein only to the degree necessary to facilitate an understanding of the novel features of the present invention.

Figure 1:
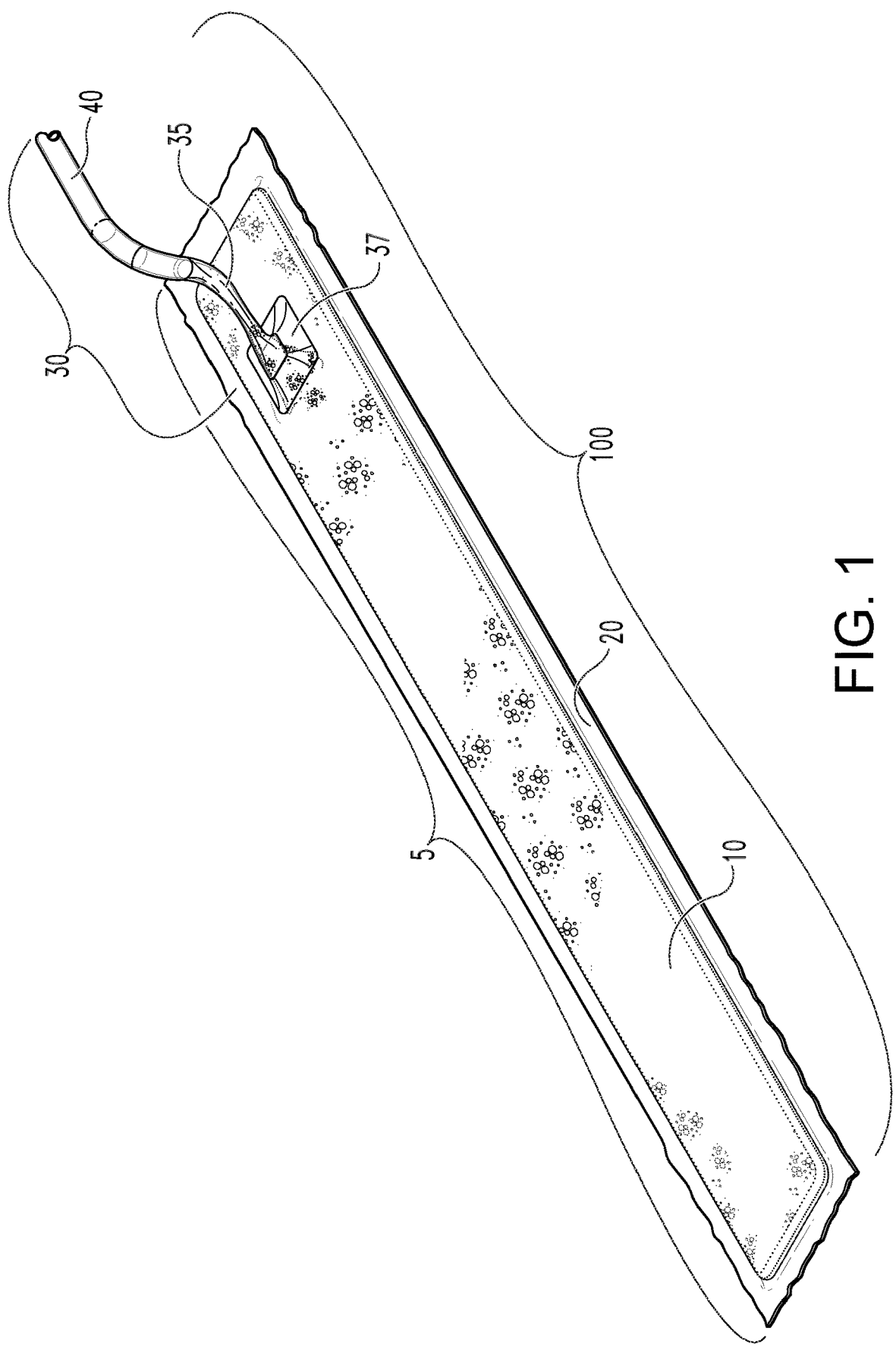
FIG. 1 is a view depicting an illustrative dressing assembly in accordance with one embodiment of the invention, comprising outstretched sponge strip, sponge, adhesive tape, and part of the suction tubing, as viewed from above.

Referring to FIG. 1, presented is an illustrative, non-limiting embodiment of a dressing assembly comprising an outstretched sponge strip, sponge, adhesive tape, and suction tubing assembled together, designated generally therein by the reference number 100 (referred to hereinafter as dressing assembly 100). This dressing assembly 100 includes several primary components, described hereinafter. Dressing assembly 100 includes a sponge strip 5. Comprised in sponge strip 5 is a sponge/porous material 10, referred to hereinafter as "sponge 10". The sponge 10 may be made of any suitable porous material commonly used in the medical arts in the treatment of wounds or incisions, such as, illustratively, porous foam. The illustrative view depicts the sponge 10 as having a uniformly elongated structure; but it is understood that, as contemplated herein, the sponge 10 may alternatively have various structures and shapes other than the elongated one depicted, depending on the type and shape of wound being treated. Also, although the illustrative planar view in FIG. 1 depicts the sponge 10 as having a flat, rectangular structure, the sponge 10 of the invention is not rectangular or flat like the sponges in existing products; instead, the sponge 10 of the invention is designed to have a geometric shape that has the tendency to create an overall vector of force inward (as discussed below), such that when the sponge 10 is positioned on a wound or incision, this shape helps draw the wound edges in, and thus take the tension off of the wound; this is even more so when a negative pressure is applied, as is described later below. Additionally, the sponge strip 5 includes an adhesive dressing or tape strip 20 (hereinafter "tape 20") that stretches out from the sponge 10 and runs along the edges of the sponge strip 5. Tape 20 is similar to the adhesive dressing or tape used in common NPWT devices; when the dressing assembly 100 is put in place, positioning sponge 10 over the wound, this adhesive tape 20 would adhere to the skin and run parallel to the wound and would provide a seal along the length of the sponge strip 5. In other words, the sponge 10 is applied by positioning it in contact with the wound or incision line, and the adhesive tape 20 is applied to the skin on both sides and on both ends of the wound. Moreover, the sponge strip 5 includes an impermeable film drape (not shown) applied or attached over the top to create a complete seal around the sponge strip 5. This film drape is similar to the film drapes used in common NPWT devices. In one variation of the invention, the film drape and the adhesive tape 20 may be the same piece of material with a narrow strip towards the edges covered with an adhesive. Also, the sponge strip 5, which comprises the sponge 10 and adhesive tape 20, may be provided in different roll forms, so as to cover various shapes and lengths of cuts and wounds (such as surgical incisions). Accordingly, sponge strips 5 may be packaged in various sizes: short, long, wide, narrow, etc. Sponge strip 5 may also be provided with a peel away deeper backing (not shown in FIG. 1), allowing easy peel-away of the backing at time of application.

Dressing assembly 100 also includes a vacuum or suction tubing 30 (hereinafter "tubing 30"). Tubing 30 may be made of any one or more suitable tubing material used in the medical arts such as the suction tubing used in common NPWT devices, such as silicone or plastic, and the like. As depicted in FIG. 1, tubing 30 comprises two parts: a length of soft, flat tubing 35 and a length of more rigid tubing 40. The lengths of tubing 35 and 40 may be a single length of tubing with one soft, flat portion on one end and a more rigid portion along the remainder of the tubing, with the soft, flat portion tapering to the more rigid portion that is more round; or, the lengths of tubing 35 and 40 may be two separate lengths of tubing coupled together, one soft and flat, the other more rigid. Suitable materials for construction of the tubing include plastic or silicone. But it is understood that rigid tubing 40 must possess sufficient rigidity to prevent collapsing under the reduced pressure used in the invention, whereas soft, flat tubing 35 is stented open as discussed below. Soft, flat tubing 35 is coupled at its free terminus to the sponge strip 5 via any of a variety of suitable coupling methods known in the art. Illustratively, one way of accomplishing the coupling of tubing 35 to the sponge strip 5 is via a coupling junction and/or interface 37 in the film drape. This allows the suction effect to pass into the sponge strip 5, and into sponge 10, when negative pressure is applied via the hand pump (as discussed below). Coupling junction and/or interface 37 of the invention may be similar to the coupling junctions and/or interfaces used in common NPWT devices, except that the coupling junction and/or interface 37 of the invention is designed to be flatter than those used in common NPWT devices, and may be constructed of soft plastic or silicone materials, or the like, thus providing the advantage over common NPWT devices of decreasing the pressure exerted on the wound area upon application of the sponge strip 5 to the wound. Additionally, soft, flat tubing 35 is stented open with a small amount of suitable sponge material, to prevent it from collapsing and closing up when vacuum is applied. The suitable sponge material with which soft, flat tubing 35 is stented open may be the same as or different than that of sponge 10 material. Soft, flat tubing 35 is the portion of tubing 30 that would come into proximity of, or may lie on top of, the wound or incision being treated; thus, the need for softness and flatness in order to decrease the pressure exerted by the tubing on the wound. For the same reason, as stated above, the coupling junction and/or interface 37 between tubing 35 and sponge strip 5 is likewise made of flat, soft material. In contrast, the commonly used round tubing in NPWT devices available on the market, as well as the coupling junctions, are made of firm plastic that can create a pressure effect and/or necrosis on the skin, and can cause damage to the skin if an ACE wrap is applied overtop, or if the patient's abdominal skin creates pressure.

Figure 2:
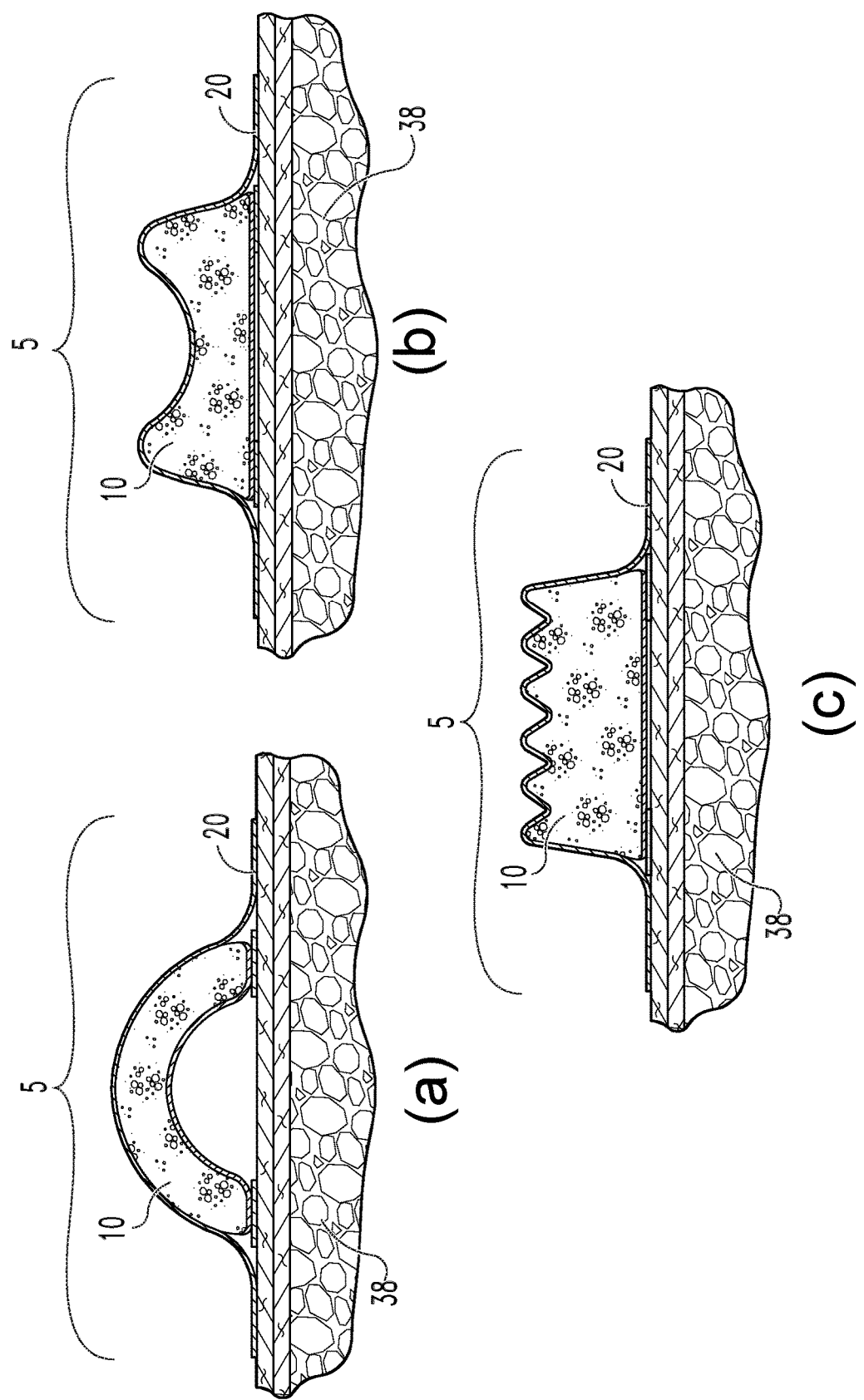
FIG. 2 depicts a lateral cross-sectional view of the various sponge shapes and tape looking down the long axis of the sponge strip: (a) sponge with a "right-side-up arch" shape; (b) sponge with an "upside-down arch" shape; (c) sponge with an "accordion" top shape.

Referring now to FIG. 2, presented are illustrative, non-limiting embodiments of a sponge strip 5 comprising examples of sponge 10 that have geometric shapes that have the tendency to create an overall vector of force inward when placed on a wound or incision. These shapes would help draw the wound edges in, and thus reduce the tension off of the wound. One such example is depicted in FIG. 2(a), showing the cross-section looking down the long axis of sponge strip 5 applied to a patient's skin 38. In this example, sponge 10 is shaped in the form of a "right-side-up arch". Another example is depicted in FIG. 2(b), which shows a sponge 10 that is shaped in the form of an "upside-down arch". The example depicted in FIG. 2(c) shows a sponge 10 that has a "pleated" top, i.e., a top that resembles an "accordion" shape. The "accordion" shape may alternatively be a part of the drape, or of the sponge 10, or of the combined drape plus sponge 10. Again, these sponge shapes provide a novel effect not previously used in the art of wound dressings, in that the shapes (similar in theory to a shaped charge used in the military) create a vector force in the direction of the midline of the wound or incision, especially when a negative pressure is applied, thus enhancing wound healing.

Figure 3:
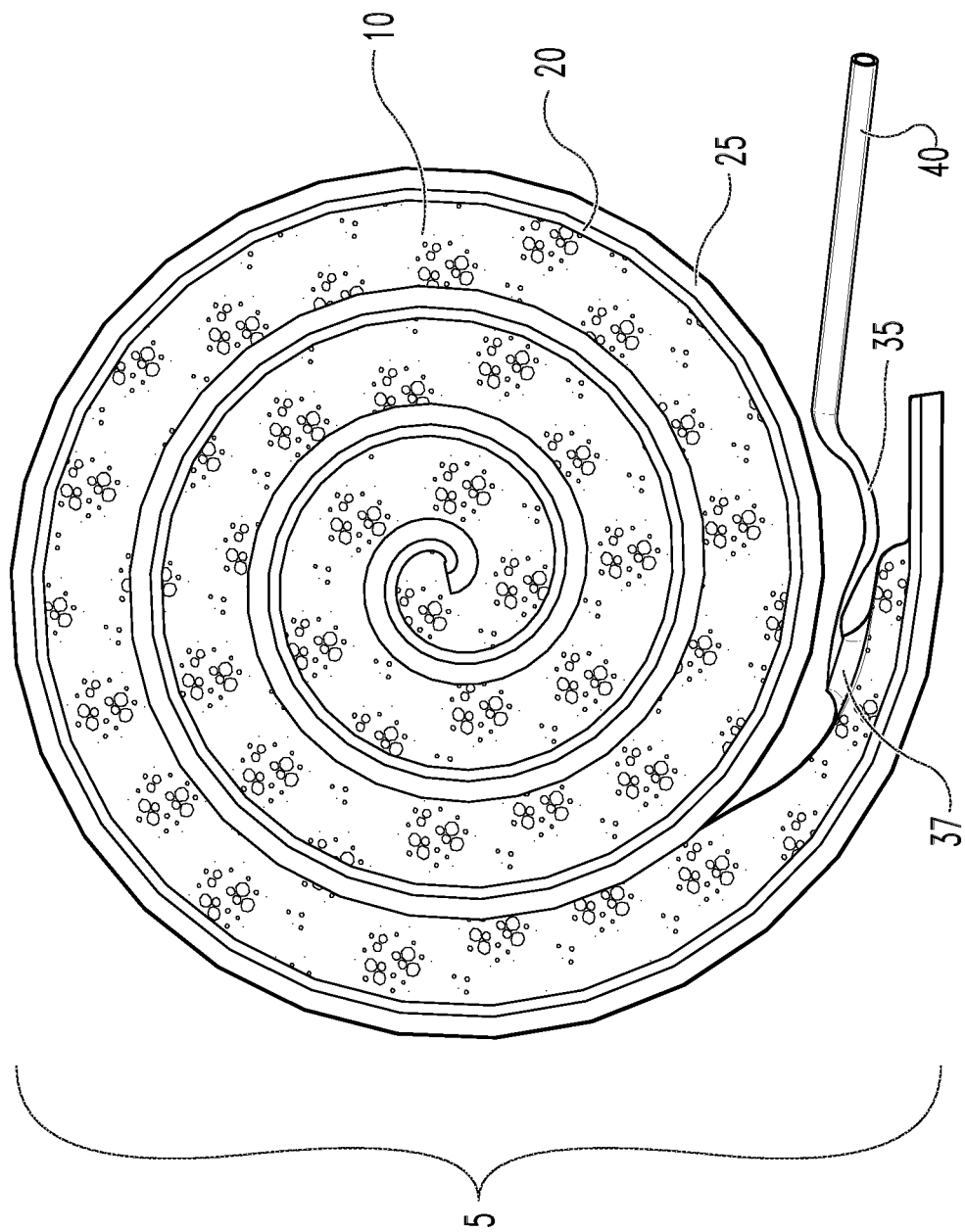
FIG. 3 depicts a side view of a rolled-up design of the sponge strip.

Referring now to FIG. 3, presented is an illustrative, non-limiting embodiment of the invention, depicting a side view of the sponge strip 5 portion of the dressing assembly 100, provided in a rolled-up "tape-like" design, which may preferably be sterile. In addition to the sponge 10 and the adhesive tape 20 of sponge strip 5, shown is a peel-away deeper backing 25, which is readily peeled away as the rolled-up sponge strip is unrolled and applied onto the wound. As discussed earlier, this rolled-up sponge strip 5 may be provided in various lengths, sizes, and shapes, and may be included as part of a sterile dispenser assembly (not shown). Illustratively, the dispenser assembly may be akin to a common tape dispenser.

Figure 4:
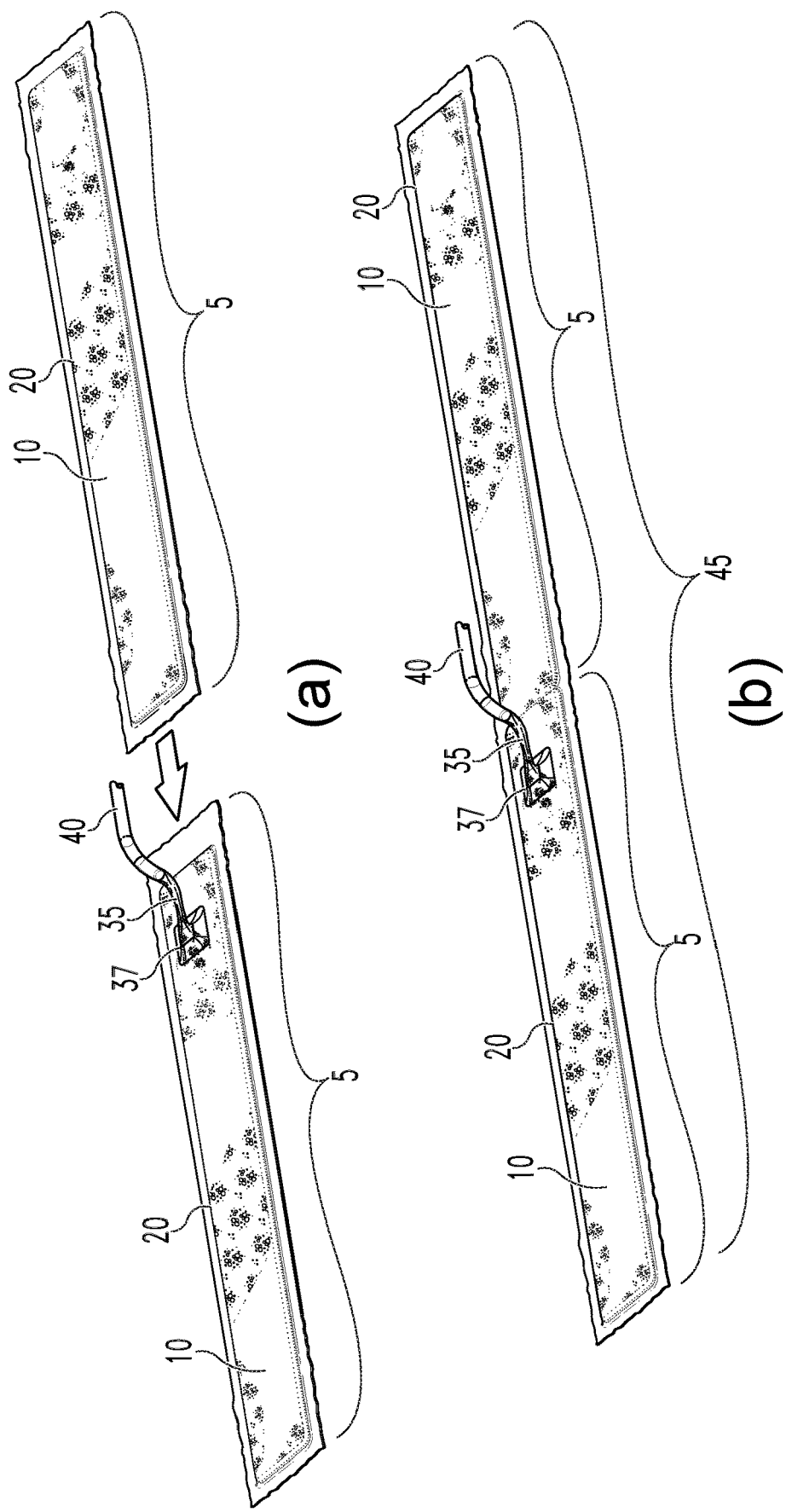
FIG. 4 is a view depicting a modular design of the outstretched sponge strip, as viewed from above, being extended in length.

Referring now to FIG. 4, presented is an illustrative, non-limiting embodiment of a modular design of the invention. In this modular design example, a sponge strip 5, shown with soft, flat tubing 35 attached via a coupling junction and/or interface 37 (see FIG. 4(a)) is lengthened ("daisy chained") via the addition of a second sponge strip 5, which may be of equal or different length, to provide a sponge strip 45 having a greater length (see FIG. 4(b)). The addition of the second sponge strip 5 may be accomplished via the use of a commercially available Tegaderm™ film dressing (not shown), and may be repeated multiple times with additional sponge strips 5 as needed. Thus, due to the extra length of the dressing roll in the "tape-like' design of the invention, one can easily modify the shape of the dressing, and also change the placement of the point at which suction is applied. The placement may be required to be changed due to, e.g., an overhanging abdominal wall, or a splint, or a brace. Moreover, in the case that a very long dressing is needed, one or more sponge strips 5 can be "daisy chained" on either end, either by applying another adherent dressing overtop (e.g., using a Tegaderm™) or by overlapping the dressings.

Figure 5:
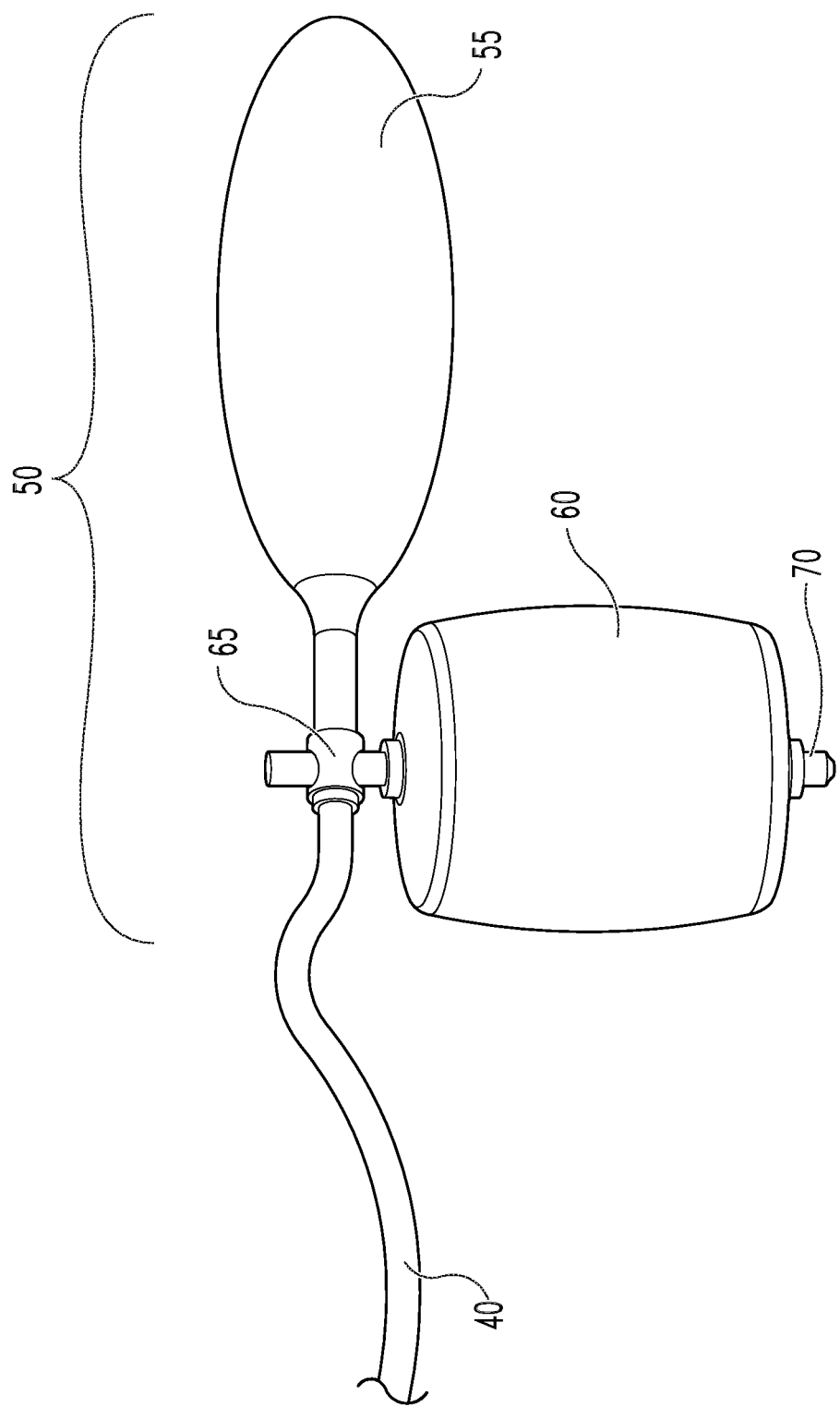
FIG. 5 is a view depicting a suction and fluid collection apparatus comprising a hand pump, a relief or control valve, and a fluid collection reservoir or canister in connection with the suction tube.

Referring now to FIG. 5, presented is an illustrative, non-limiting embodiment of the invention, depicting a sketch of a suction and fluid collection apparatus 50 (hereinafter "apparatus 50") with one end of the suction tubing 40 attached to a valve 65. Apparatus 50 comprises a hand pump 55, a collection canister or reservoir 60, and a valve 65. In one variation of the invention, reservoir 60 includes a stoppable opening or nozzle 70 at its bottom, which serves as the port via which the reservoir is emptied. Valve 65 may be any valve of various available valves known in the art in which the lower and upper pressure limits are pre-set or can be manually set by the physician, medical professional, care provider, or patient. For the purpose of the invention herein, the lower and upper pressure limits of the valve may be in the range between about −20 mmHg and about −250 mmHg; more preferably between about −120 mmHg and about −150 mmHg. The valve is designed to "blow out" if the reduced pressure should exceed the desired upper negative pressure limit value, and to make an audible sound if the reduced pressure drops below the desired lower negative pressure limit value. Also, the valve may be any suitable one-way valve that prevents leakage of the pressure gradient and also prevents fluid back-flow into the wound. Hand pump 55 may be any one of available hand pumps known in the art, such as the hand pump (rubber bulb) of a stethoscope; it may include a one-way valve (not shown) on the opposite end that lets air out when the bulb is squeezed, but does not let air back in. In one configuration, the apparatus 50 may be assembled so that the hand pump 55, the reservoir 60, and the suction tubing 40 are all connected to the valve 65. Alternatively, in another configuration, the reservoir 60 may be attached instead at a point in suction tubing 40 via a "T" connector (not shown in FIG. 5). Also, alternatively, the valve 65, hand pump 55, and collection reservoir 60 may be of any types and/or may be connected together in any configuration or manner that allows: (a) the application and maintaining of the desired negative pressure gradient; (b) pulling of the fluid and moisture into the reservoir; and, (c) preventing fluid from collecting into the hand bulb (such as in the case where a rubber bulb is used as the hand pump). For example, this may be accomplished by having the patient charge the system (e.g., squeeze the hand bulb) at the same time as emptying the reservoir. The hand bulb can also be a "pass-through" bulb, e.g., similar to a turkey baster bulb, but instead of a closed end, both ends would be open; the end coming from the patient to the bulb/reservoir would have a one-way or duck-bill valve; the other end would be the outflow valve; thus, when charged by the patient, the fluid can only pass out of the system and into the reservoir; the outflow end can then be capped and pumped to the desired pressure.

In the following, additional alternative illustrative designs of the invention are provided, depicted in the drawings of FIG. 6-FIG. 10.

Figure 6:
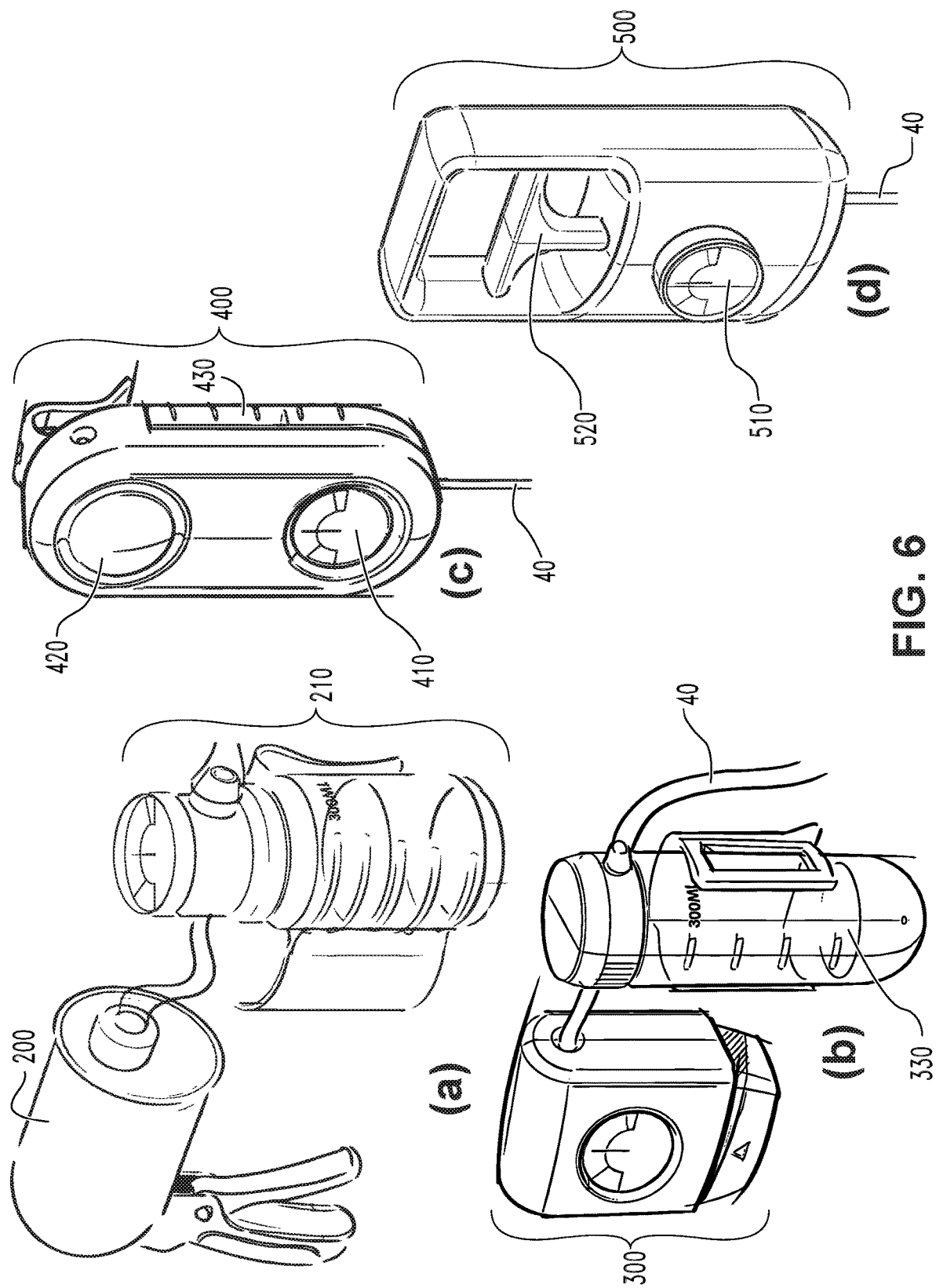
FIG. 6 is a schematic that shows four different, illustrative, non-limiting designs (a), (b), (c), and (d) for the pumping and collection components of the invention comprising different types of hand actuated pump and collection canister, as well as a valve, and a pressure gauge.

Referring now to FIG. 6, presented are illustrative, non-limiting embodiments of the invention, depicting four different designs (a), (b), (c), and (d) that include the pumping and collection components of the invention and comprise different types and configurations of the hand actuated pump, collection canister, valve, and pressure gauge.

Referring now to FIG. 7, represented is a schematic that shows the design of FIG. 6(a) as illustratively being used in conjunction with a suction tubing and dressing assembly of the invention applied to the knee wound or incision of a patient (see FIG. 7(a)). In this design (see FIG. 6(a) and FIG. 7(b)), a hand pump 200 is used of the type known in the art as a "pistol grip" hand pump (or the "Ambu® Res-Cue" type of hand pump). Included in this design is an apparatus 210 that comprises an enclosed, internal valve (not shown), a pressure gauge 220 with a blowout valve (not shown), a nozzle 225 via which connecting to tubing 40 is done, and a collection canister 230 (e.g., a custom molded catch-can/vacuum chamber) for collection of any possible fluid exudates from the wound or incision. Collection canister 230 may optionally have an openable port at the bottom (not shown) for easy emptying when needed. Alternatively, or in addition to the openable port, collection canister 230 may optionally be threaded for easy opening by twisting off, if desired; it may be designed to be disposable, or designed to be reused. Pressure gauge 220 may optionally include a green "go, no go" reading that indicates the range for optimal negative pressure (see below). The apparatus 210 also includes a belt clip 235 to allow convenient attachment of the apparatus 210 to the belt of the user, and a suitably sized "dock" (or "holster") 240 for placement of the hand pump 200 when not in use (see FIG. 7(c)). The hand pump 200 is connected via a length of tubing 250 to the internal valve. The internal valve may be any of the known types in the art designed to keep any fluid exudates from progressing into the pressure gauge 220 and/or hand pump 200, and is designed to function in a wet environment in the event that exudate fluid interacts with the pressure gauge. Functionally, as depicted in FIG. 7(a), the dressing assembly is applied to the wound or incision as discussed in the foregoing, and is connected to the apparatus 210 via interface 37 and tubing 35 and 40, the pump is actuated by hand, squeezing the "pistol grip" to the proper negative pressure, as indicated by the pressure gauge. In the case of over-pressurizing, the blowout valve would relieve the extra pressure to bring it to within the optimal range. In the case of under-pressurizing to below the allowable range, a bell or other mechanical audible sound occurs that prompts the user to use the hand pump to bring the pressure back to within the optimal range. As discussed in the forgoing, the reduced pressure in NPWT devices may be in the range between about −20 mmHg and about −250 mmHg, and the optimal (i.e., preferred) reduced pressure may be in the range of between about −120 mmHg and about −150 mmHg.

In the following discussion regarding the designs depicted in FIG. 8, FIG. 9, and FIG. 10, it is to be understood that these additional embodiments of the invention are similar in many ways to the design represented in FIG. 7 discussed above. Accordingly, the designs depicted in FIG. 8, FIG. 9, and FIG. 10 will only be discussed to the extent required, especially to point out their differences relative to the design depicted in FIG. 7. However, functionally they are very similar to the design of FIG. 7.

Referring now to FIG. 8, represented is a schematic that shows the design of FIG. 6(b) as illustratively being used in conjunction with a suction tubing and dressing assembly of the invention applied to the knee wound or incision of a patient (see FIG. 8(a)). In this design (see FIG. 6(b) and FIG. 8(c)), an apparatus 300 houses together the internal valve (not shown), a pressure gauge 310 and blowout valve (not shown), and a multi-finger hand pump 320 at the bottom. The pressure gauge is located on the hand pump to enable quick check when pressurizing. Hand pump 320 is actuated by grasping the apparatus 300 and squeezing the pump upwards with the fingers into the apparatus as needed, as depicted in FIG. 8(b), to bring the negative pressure to within the optimal range. For collection of any fluid exudates from the wound, a canister 330 is provided. Canister 330 is essentially a twist-off catch can or vacuum chamber, and is provided with a threaded cap 335. The internal valve in apparatus 300 is connected to the threaded cap 335 via a length of tubing 340. Threaded cap 335 includes a nozzle 345 via which connection to tubing 40 is done. The canister 330 may be fitted with a belt clip for easy attachment to the belt of the user. The design of FIG. 8 may also conveniently include a waist belt 355, with adjustable length via a Velcro® type fastener, and custom plastic clips to hold components.

Referring now to FIG. 9, represented is a schematic that shows the design of FIG. 6(c) as illustratively being used in conjunction with a suction tubing and dressing assembly of the invention applied to the knee wound or incision of a patient (see FIG. 9(a)). In this design (see FIG. 6(c) and FIG. 9(b)), a single-body apparatus 400 houses together the internal valve (not shown), a pressure gauge 410 and blowout valve (not shown), a soft rubber push hand pump 420, and a collection canister 430 (e.g., a custom molded "catch can/vacuum chamber"). As shown in FIG. 9(b), canister 430 is attached to the back of apparatus 400, and is detachable for easy emptying or disposal. Connection of the components via tubing is similar to that of the foregoing designs, but is enclosed in the single-body apparatus 400. Apparatus 400 may also be fitted with a belt clip 440 for easy attachment to the belt of a patient. Hand pump 420 is actuated by squeezing/pressing the soft rubber, as depicted in FIG. 9(c), to bring the negative pressure to within the optimal range. The design depicted in FIG. 9 has an advantage over the designs depicted in FIG. 7 and FIG. 8, in that it conveniently houses the hand pump, collection canister, internal valve, gauge and blowout valve, and connecting tubing all in one apparatus, making it easier for the patient to carry and use.

Figure 10:
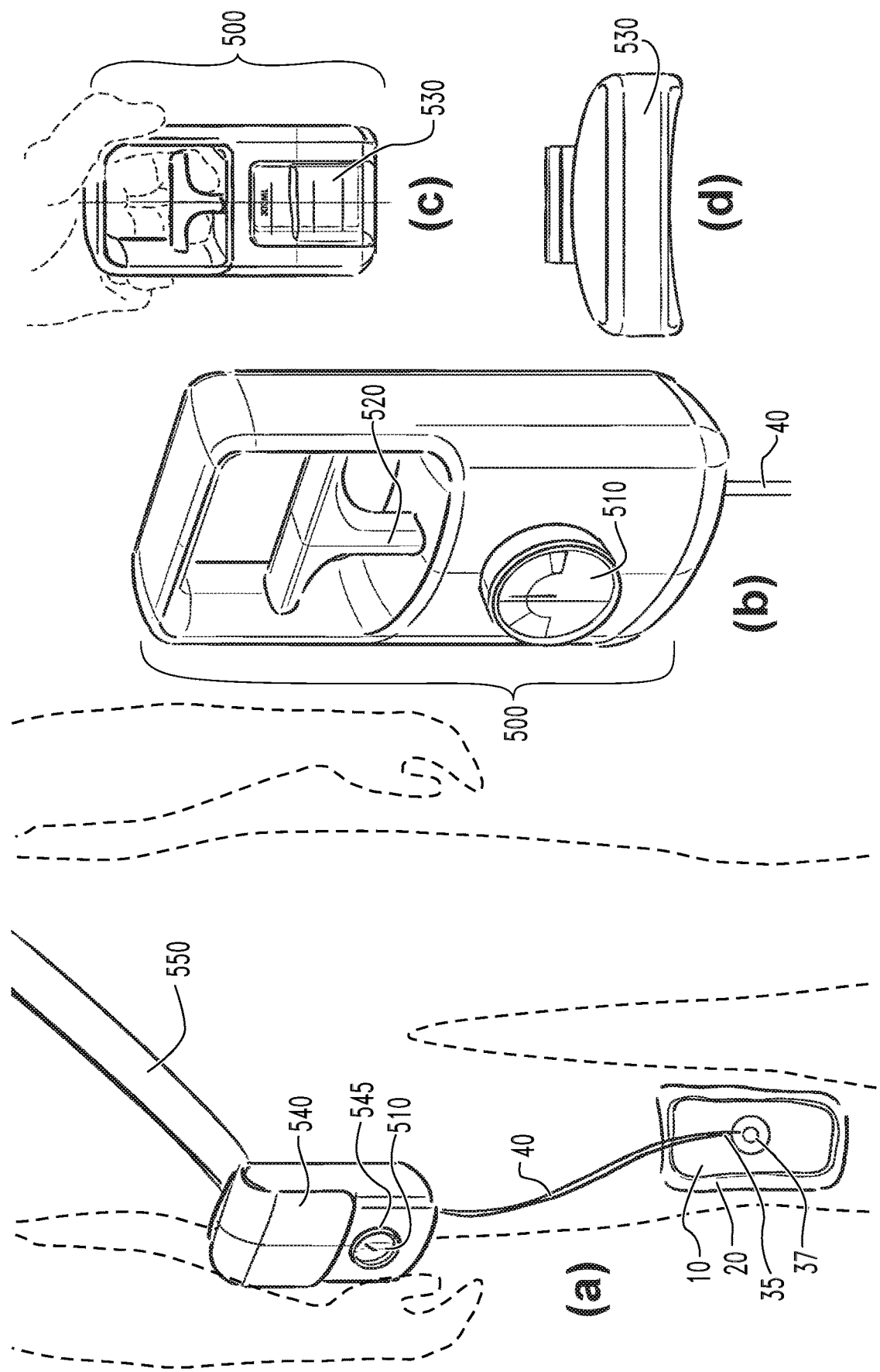
FIG. 10 is a schematic that shows the design of FIG. 6(d) as illustratively being used in conjunction with a suction tubing and dressing assembly of the invention applied to the knee wound of a patient.

Referring now to FIG. 10, represented is a schematic that shows the design of FIG. 6(d) as illustratively being used in conjunction with a suction tubing and dressing assembly of the invention applied to the knee wound or incision of a patient (see FIG. 10(a)). In this design (see FIG. 6(d) and FIG. 10(b)), a single-body apparatus 500 houses together the internal valve (not shown), a pressure gauge 510 and blowout valve (not shown), a "pull-up" hand pump 520, and a collection canister 530 (e.g., a custom molded "catch can/vacuum chamber"). The "pull-up" hand pump 520 is similar to art-known hand pumps, such as the Medical Sputum Aspirator manual suction pump. As shown in FIG. 10(c), canister 530 is attached to the back of apparatus 500, and is detachable for easy emptying or disposal. Canister 530 may also be designed to have a curved back housing for ergonomics when held close to the patient's waist (see FIG.

10(*d*)). Connection of the components via tubing is similar to that of the foregoing designs, but is enclosed in the single-body apparatus 500. In this design, hand pump 520 is actuated by pulling the two-fingered lever up, as depicted in FIG. 10(*c*), to bring the negative pressure to within the optimal range. In addition, apparatus 500 may be provided with a properly sized satchel 540 (see FIG. 10(*a*)) with a "lift-top" for quick access to the hand pump. Satchel 540 may optionally have a shoulder strap 550 (or alternatively a waist belt, or a belt clip) for easy portability by the patient. For convenience, the satchel has a hole 545 properly located and sized in the satchel for the pressure gauge 510 to stick through, allowing the patient to readily check the pressure gauge.

While the four designs depicted in FIG. 7-FIG. 10 have several different features in regard to the types of hand pump and collection canister shown, as well as to the methods of portability, it is to be understood that, as contemplated herein, these features can readily be interchanged between the four depicted designs, to come up with a number of additional similar designs. Nonetheless, in all of these designs, it is to be understood that, as contemplated herein, the features regarding the internal valve, the pressure gauge, and the blowout valve are similar. Thus, the pressure gauge may have a green "go, no go" display (or reading) that indicates the pressure range for optimal healing, and is designed to function in a wet environment in the event that fluid interacts with the gauge; the blowout valve will relieve the excess negative pressure back to within the optimal range if over-pressurizing occurs; and, when the pressure range falls below the allowable range, a bell or other mechanical sound will occur prompting the user to use the hand pump to restore the reduced pressure to within the optimal range. It is also to be understood that, as contemplated herein, numerous alternative configurations of the components of the above designs are possible. Illustratively, one can configure the components in all the above designs in such a manner that the collection canister is connected by attachment at a point in suction tubing 40 via, e.g., a "T" connector; or, tubing 40 may be connected directly to one nozzle/opening in the internal valve while the collection canister may be connected directly or via another length of tubing to another nozzle/opening in the internal valve. In another example, the internal valve and the blowout valve in all the above designs may be designed to be one and the same valve instead of being two separate valves.

In another embodiment of the invention, provided herein are kits that comprise some or all the parts of the various designs described in the preceding paragraphs of the Detailed Description section, pre-assembled and pre-packaged, preferably under sterile conditions, and ready for use.

In another embodiment of the invention, disclosed herein is a method of use of the negative pressure wound apposition dressing, device, and/or system described in the foregoing embodiments to treat a wound and promote healing. The method of use comprises one or more of the following steps:

(a) obtaining a sponge strip comprising a sponge portion, an adhesive tape portion running along the edges, an impermeable drape, and a coupling junction or interface for connecting a suction tubing; wherein the sponge is shaped so as to create a vector force inward, such as one wherein the lateral cross section has a shape selected from: a right-side-up arch and an upside-down arch, either of which may be topped with an "accordion" shape; and wherein the coupling junction or interface is flat and soft;

(b) connecting one end of a length of suction tubing at the coupling junction or interface, wherein the portion of the suction tubing that attaches at the coupling junction or interface is soft and flat and is stented with a small amount of sponge material;

(c) connecting the other end of the suction tubing to a pressure relief valve to which is also connected a hand pump and a reservoir; or, the reservoir may instead be connected at a point in the suction tubing via a "T" connector;

(d) optionally, attaching one or more additional sponge strips via Tegaderm™ to increase the length of the sponge strip and obtain a longer sponge strip that has a length suited for the wound being treated; wherein the one or more additional sponge strips do not include a coupling junction or interface;

(e) preparing the wound area for application of a dressing using standard wound preparation methods known in the art;

(f) applying the sponge strip to a wound area so that the tape portion adheres to the skin around the wound and provides a seal;

(g) squeezing the hand bulb to create suction and reduce the pressure to be in a desired range;

(h) maintaining and/or restoring the reduced pressure as needed by use of the hand bulb;

(i) periodically emptying the reservoir as needed;

until sufficient healing of the wound has been achieved, and removal of the dressing becomes advisable.

In another embodiment of the invention, disclosed herein is a method of use of the negative pressure wound apposition kit described in the foregoing to treat a wound. This method of use comprises one or more of the following steps:

(a) preparing the wound area for application of a dressing using standard wound preparation methods known in the art;

(b) removing the packaging from the kit;

(c) applying the sponge strip of the kit to the wound area so that the tape portion adheres to the skin around the wound and provides a seal;

(d) optionally, attaching one or more additional sponge strips via Tegaderm™ to increase the length of the sponge strip and obtain a longer sponge strip that has a length suited for the wound being treated;

(e) squeezing the hand bulb to create suction and reduce the pressure to be in a desired range;

(f) maintaining and/or restoring the reduced pressure as needed by use of the hand bulb;

(g) periodically emptying the reservoir as needed;

until sufficient healing of the wound has been achieved, and removal of the dressing becomes advisable.

In another embodiment of the invention, provided herein is a flexible wound apposition dressing assembly useful for promoting closure and healing of surgical, non-surgical, and traumatic wounds, said dressing assembly comprising a sponge strip that includes a sponge portion, an adhesive tape portion that extends out from the sponge portion and runs along the edges the sponge portion, and an impermeable drape that completely covers the sponge portion and adhesive tape portion of said dressing assembly; wherein the sponge portion has a geometric shape that creates an overall vector of force inward when placed on a wound and helps draw the wound edges inwardly towards each other, where said geometric shape of the sponge portion is selected from one in which the lateral cross section of the sponge portion resembles a right-side-up arch, one in which the lateral cross section of the sponge portion resembles an upside-down arch, and one in which the lateral cross section of the sponge portion has a top that resembles the pleats of an accordion. In another aspect, the sponge of the sponge portion is made of a porous material suitable for wound treatment. In another aspect, the impermeable drape and the adhesive tape portion may be the same piece of material with a narrow strip towards the edges covered with an adhesive. In another aspect, the sponge strip may further comprise a peel-away deeper backing for easy peeling away prior to placement on a wound. In another aspect, the dressing assembly may be further provided in a rolled-up form in various lengths. In another aspect, the rolled-up form of the dressing assembly may be provided in a tape-like dispenser device. In another variation of the invention, the flexible wound apposition dressing assembly may be further modified modularly by attachment of one or more additional wound apposition dressing assemblies, to obtain a lengthened wound apposition dressing assembly; where the attachment of the one or more additional wound apposition dressing assemblies is accomplished either by overlapping the ends of the respective sponge strips together or by using one or more Tegaderms™; wherein the one or more additional wound apposition dressing assemblies are of the same or different lengths. In another aspect, the flexible wound apposition dressing assembly further comprise a coupling interface in the film drape, and also comprise a length of soft, flat tubing having one end penetrating sealably through the coupling interface and projecting into the sponge portion of the sponge strip and the other end of the soft, flat tubing coupled to one end of a length of rigid tubing; wherein the coupling interface is flat and made of soft material so as to minimize pressure when the dressing assembly is applied to a wound; and, wherein the soft, flat length of tubing is stented open with a small amount of sponge material. In another aspect, the coupling interface and the length of soft, flat tubing are designed such that they do not cause necrosis of the skin when said dressing assembly is applied to the wound of a patient.

In another embodiment of the invention, provided herein is a negative pressure wound apposition dressing system, said system comprising the flexible wound apposition dressing assembly described above, and further comprising a suction and fluid collection apparatus designed for use within a preset negative pressure range, wherein said suction and fluid collection apparatus includes a fluid collection canister, a first valve, a hand actuated suction pump, and a pressure gauge that includes a second valve; wherein the fluid collection canister is connected via an opening to the free end of the length of rigid tubing, and via another opening to the first valve; wherein the first valve is connected to the hand actuated suction pump, and wherein the first valve is also connected to the pressure gauge; and wherein the second valve is designed to blow out if the upper limit of the preset negative pressure range is exceeded and to make an audible noise if the pressure drops below the lower limit of the preset negative pressure range. In one alternative design, the first valve and the second valve may be designed to be one and the same valve. In one aspect, the negative pressure wound apposition dressing system has a preset negative pressure range between about −20 mmHg and about −250 mmHg, but preferably between about −120 mmHg and about −150 mmHg. In another aspect, the pressure gauge includes a green "go, no go" display that indicates the range for the preset pressure range. In another aspect, the first valve is designed to function in a wet environment in the event fluid interacts with the pressure gauge. In another aspect, the fluid collection canister is disposable. In another aspect, the negative pressure wound apposition dressing system is completely mechanical and does not include any electronic components. In another aspect, the negative pressure wound apposition dressing system may further comprise means for easy portability by the patient of the suction and fluid collection apparatus, wherein said means for easy portability include the use of clips, waist belts, or shoulder straps, and may also further include the use of a satchel.

In another embodiment of the invention, provided herein is a method of use of the negative pressure wound apposition dressing system described above to treat a wound of a patient, said method comprising the steps of: (a) preparing the wound area for application of the flexible wound apposition dressing assembly using standard wound preparation methods known in the art; (b) applying the sponge strip along the length of the wound so that the sponge portion lies over the wound and the adhesive tape portion adheres to the skin surrounding the wound; (c) using the hand pump to bring the negative pressure to within the optimum pressure range; (d) further using the hand pump as needed to maintain the negative pressure within the optimum pressure range; (e) disposing of any fluid exudates that collect in the fluid collection canister as needed; and, (f) repeating steps (c)-(e) as needed; resulting in healing of the wound of the patient.

While the disclosure has been illustrated and described in detail in the figures and foregoing description, the same is to be considered as illustrative and not restrictive in character, it being understood that only selected embodiments have been shown and described and that all changes, modifications and equivalents that come within the spirit of the disclosures described heretofore and/or defined by the following claims are desired to be protected. It is understood that additions, omissions, substitutions, and other modifications can be made by those skilled in the art without departing from the scope of the present invention.

What is claimed is:

1. A flexible wound apposition dressing assembly useful for promoting closure and healing of surgical, non-surgical, and traumatic wounds treated with negative pressure therapy, said dressing assembly comprising:
    a sponge strip that includes a sponge portion, an adhesive tape portion that extends out from the sponge portion and runs along the edges of the sponge portion, and an impermeable drape that completely covers the sponge portion and the adhesive tape portion of said dressing assembly;
    a soft, generally flat flexible vacuum interface connected to the sponge portion;
    vacuum tubing extending from a vacuum source and connected to the vacuum interface;
    a sponge stent connected to the vacuum interface for preventing collapse of the same;
    wherein the sponge portion has a semi-circular geometric shape that arches over a wound to generate an overall vector of force inward when placed on the wound to draw the wound edges inwardly towards each other;
    wherein application of negative pressure to the sponge portion increases the overall vector of force on the wound to draw the edges inwardly towards each other.

2. The flexible wound apposition dressing assembly of claim 1, further modified modularly by attachment of at least one additional wound apposition dressing assembly to the flexible wound apposition dressing assembly, to obtain a lengthened wound apposition dressing assembly; where the attachment of the at least one additional wound apposition dressing assembly is accomplished either by overlapping the ends of the respective sponge strips together or by using one or more transparent medical dressings; wherein the at least one additional wound apposition dressing assembly are of different lengths.

3. The flexible wound apposition dressing assembly of claim 1, wherein the soft, generally flat flexible vacuum interface further comprises a length of soft, flat tubing having one end penetrating sealably through sponge portion of the sponge strip and the other end of the soft, flat tubing coupled to one end of a length of rigid tubing; wherein the interface is flat and made of soft material so as to minimize pressure when the dressing assembly is applied to a wound.

4. A negative pressure wound apposition dressing system, said system comprising the flexible wound apposition dressing assembly of claim 3, and further comprising a suction and fluid collection apparatus for use within a preset negative pressure range, wherein said suction and fluid collection apparatus includes a fluid collection canister, a first valve, a hand actuated suction pump, and a pressure gauge that includes a second valve; wherein the fluid collection canister is connected via an opening to the free end of the length of rigid tubing, and via another opening to the first valve; wherein the first valve is connected to the hand actuated suction pump, and wherein the first valve is also connected to the pressure gauge; and wherein the second valve has predetermined lower and upper pressure limits within which it is functional.

5. The negative pressure wound apposition dressing system of claim 1, where said preset negative pressure range is between about −120 mmHg and about −150 mmHg.

6. The negative pressure wound apposition dressing system of claim 4, wherein the pressure gauge includes display that indicates the range for the preset pressure range.

7. The negative pressure wound apposition dressing system of claim 4, wherein the first valve is designed to function in a wet environment in the event fluid interacts with the pressure gauge.

8. The negative pressure wound apposition dressing system of claim 4, wherein said negative pressure wound apposition dressing system is completely mechanical and does not include any electronic components.

9. The wound apposition dressing assembly of claim 3, wherein said coupling interface and said length of soft, flat tubing are designed such that they do not cause necrosis of the skin when said dressing assembly is applied to the wound of a patient.

10. The negative pressure wound apposition dressing system of claim 4, further comprising means for easy portability by the patient of the suction and fluid collection apparatus.

11. The negative pressure wound apposition dressing system of claim 10, wherein said means for easy portability include the use of clips, waist belts, or shoulder straps.

12. The negative pressure wound apposition dressing system of claim 11, wherein said means for easy portability further include the use of a satchel.

13. A method of use of the negative pressure wound apposition dressing system of claim 4 to treat a wound area of a patient, said method comprising the steps of:
(a) preparing the wound area for application of the flexible wound apposition dressing assembly;
(b) applying the sponge strip along the length of the wound so that the sponge portion lies over the wound and the adhesive tape portion adheres to the skin surrounding the wound, wherein the sponge portion applies a biasing force to the wound, urging the wound edges towards one another;
(c) using the hand pump to generate negative pressure over the wound to within the optimum pressure range;
(d) further using the hand pump as needed to maintain the negative pressure within the optimum pressure range;
(e) disposing of any fluid exudates that collect in the fluid collection canister as needed;
(f) repeating steps (c)-(e) as needed;
resulting in healing of the wound of the patient.

14. A wound dressing assembly for use with a negative pressure wound treatment system, comprising:
an elongated sponge portion having an arcuate cross-sectional semi-circular geometric shape that arches over a wound to generate an overall vector of force inward when placed on the wound to draw the wound edges inwardly towards each other;
wherein application of negative pressure to the sponge portion increases the overall vector of force on the wound to draw the edges inwardly towards each other;
an adhesive tape portion extending from the sponge portion; and an impermeable drape portion disposed to completely covers the sponge portion and the adhesive tape portion;
a soft, flat length of flexible tubing coupled to the elongated sponge portion to define an interface;
a sponge stent positioned in the soft, flat length of flexible tubing to prevent collapse and maintain pneumatic communication therethrough.

15. The wound dressing assembly of claim 14 and further comprising:
a manually powered vacuum pump; and
a length of rigid tubing connecting the manually powered vacuum pump to the soft, flat length of flexible tubing.

16. The wound dressing assembly of claim 15 wherein the elongated sponge portion is secured over a wound; wherein the elongated sponge portion provides a biasing force to urge the wound closed; wherein energization of the manually powered vacuum pump yields a negative pressure environment over the wound; and wherein the negative pressure environment increases the biasing force.

17. A method of applying negative pressure and a biasing force to treat a wound area of a patient, comprising:
(a) preparing a wound area for application of an elongated flexible wound apposition dressing assembly;
(b) applying an elongated sponge strip, having an arcuate cross-sectional semi-circular geometric shape that arches over a wound, along the length of the wound so that the sponge portion extends over the wound and is adhered to skin surrounding the wound, wherein the sponge strip applies a biasing force to the wound, urging the wound edges towards one another;
(c) connecting a vacuum pump to the elongated sponge strip;
(d) manually energizing the vacuum pump to generate negative pressure over the wound wherein application of negative pressure to the sponge portion increases the overall vector of force on the wound to draw the edges inwardly towards each other;
(e) further manually energizing the vacuum pump to maintain the negative pressure within a predetermined pressure range;
(f) disposing of any fluid exudates that collect in a fluid collection canister;
(g) repeating steps (d)-(f) as needed;
wherein in step (c) the vacuum pump is connected in fluidic communication with a soft, flat length of flexible tubing coupled to the elongated sponge strip; and a sponge stent is positioned in the soft, flat length of flexible tubing to prevent collapse and maintain fluidic communication therethrough.

\* \* \* \* \*